(12) United States Patent
Krishnan et al.

(10) Patent No.: US 9,921,104 B2
(45) Date of Patent: Mar. 20, 2018

(54) SIMULTANEOUS MULTI-ANGLE SPECTROSCOPY

(71) Applicant: KLA-Tencor Corporation, Milpitas, CA (US)

(72) Inventors: Shankar Krishnan, Santa Clara, CA (US); Alexander Buettner, Weilburg (DE); Kerstin Purrucker, Fliederweg (DE); David Y. Wang, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/344,825

(22) Filed: Nov. 7, 2016

(65) Prior Publication Data

US 2017/0356800 A1     Dec. 14, 2017

Related U.S. Application Data

(60) Provisional application No. 62/348,870, filed on Jun. 11, 2016.

(51) Int. Cl.
*G01J 3/40*     (2006.01)
*G01J 3/18*     (2006.01)
(Continued)

(52) U.S. Cl.
CPC ............. *G01J 3/189* (2013.01); *G01J 3/0289* (2013.01); *G01J 3/10* (2013.01); *G01J 3/2803* (2013.01);
(Continued)

(58) Field of Classification Search
CPC .................... G01J 3/00; G01J 3/28; G01J 3/26
See application file for complete search history.

(56) References Cited

U.S. PATENT DOCUMENTS 5,166,752 A     11/1992    Spanier et al.
5,608,526 A     3/1997    Piwonka-Corle et al.
(Continued)

FOREIGN PATENT DOCUMENTS

WO     2015000673 A1     1/2015

OTHER PUBLICATIONS

Henault, Francois et al., "Optical design of a multi-resolution, single shot spectrograph," arXiv:1607.02357 [physic.ins-det], submitted Jul. 2016.
(Continued)

*Primary Examiner* — Abdullahi Nur
(74) *Attorney, Agent, or Firm* — Spano Law Group; Joseph S. Spano

(57) ABSTRACT

Methods and systems for performing simultaneous spectroscopic measurements of semiconductor structures over a broad range of angles of incidence (AOI), azimuth angles, or both, are presented herein. Spectra including two or more sub-ranges of angles of incidence, azimuth angles, or both, are simultaneously measured over different sensor areas at high throughput. Collected light is linearly dispersed across different photosensitive areas of one or more detectors according to wavelength for each subrange of AOIs, azimuth angles, or both. Each different photosensitive area is arranged on the one or more detectors to perform a separate spectroscopic measurement for each different range of AOIs, azimuth angles, or both. In this manner, a broad range of AOIs, azimuth angles, or both, are detected with high signal to noise ratio, simultaneously. This approach enables high throughput measurements of high aspect ratio structures with high throughput, precision, and accuracy.

21 Claims, 9 Drawing Sheets

(51) Int. Cl.
  *G01N 21/25* (2006.01)
  *G01N 21/27* (2006.01)
  *G01J 3/28* (2006.01)
  *G01J 3/02* (2006.01)
  *G01J 3/10* (2006.01)
  *G01N 33/00* (2006.01)

(52) U.S. Cl.
  CPC .......... *G01N 21/255* (2013.01); *G01N 21/27* (2013.01); *G01N 33/00* (2013.01); *G01N 2033/0095* (2013.01)

(56) References Cited

U.S. PATENT DOCUMENTS

| | | | |
|---|---|---|---|
| 5,808,738 | A | 9/1998 | Garcia-Rubio |
| 5,859,424 | A | 1/1999 | Norton et al. |
| 6,429,943 | B1 | 8/2002 | Opsal et al. |
| 6,633,831 | B2 | 10/2003 | Nikoonahad et al. |
| 6,734,967 | B1 | 5/2004 | Piwonka-Corle et al. |
| 6,816,570 | B2 | 10/2004 | Janik et al. |
| 6,859,278 | B1 | 2/2005 | Johs et al. |
| 6,895,075 | B2 | 5/2005 | Yokhin et al. |
| 6,972,852 | B2 | 12/2005 | Opsal et al. |
| 7,478,019 | B2 | 1/2009 | Zangooie et al. |
| 7,755,764 | B2 | 7/2010 | Kwak et al. |
| 7,826,071 | B2 | 11/2010 | Shchegrov et al. |
| 7,907,264 | B1 | 3/2011 | Krishnan |
| 7,929,667 | B1 | 4/2011 | Zhuang et al. |
| 7,933,026 | B2 | 4/2011 | Opsal et al. |
| 8,860,937 | B1 | 10/2014 | Dziura et al. |
| 9,291,554 | B2 | 3/2016 | Kuznetsov et al. |
| 9,310,290 | B2 | 4/2016 | Wang et al. |
| 2006/0066837 | A1* | 3/2006 | Ortyn .................. C12Q 1/6816 356/73 |
| 2007/0229852 | A1 | 10/2007 | Wack et al. |
| 2009/0279090 | A1 | 11/2009 | Wolf et al. |
| 2012/0250032 | A1 | 10/2012 | Wilde et al. |
| 2013/0114085 | A1 | 5/2013 | Wang et al. |
| 2013/0321810 | A1 | 12/2013 | Wang et al. |
| 2014/0111791 | A1 | 4/2014 | Manassen et al. |
| 2014/0166862 | A1* | 6/2014 | Flock ................. G01N 21/9501 250/208.2 |
| 2014/0172394 | A1 | 6/2014 | Kuznetsov et al. |
| 2014/0222380 | A1 | 8/2014 | Kuznetsov et al. |
| 2014/0297211 | A1 | 10/2014 | Pandev et al. |
| 2014/0316730 | A1 | 10/2014 | Shchegrov et al. |
| 2014/0375983 | A1 | 12/2014 | Wolf et al. |
| 2015/0042984 | A1 | 2/2015 | Pandev et al. |
| 2015/0046118 | A1 | 2/2015 | Pandev et al. |
| 2015/0153165 | A1 | 6/2015 | Liu et al. |
| 2015/0193926 | A1 | 7/2015 | Berlatzky et al. |
| 2015/0204664 | A1 | 7/2015 | Bringoltz et al. |
| 2015/0285735 | A1 | 10/2015 | Wang et al. |
| 2016/0161245 | A1 | 6/2016 | Fu et al. |

OTHER PUBLICATIONS

International Search Report dated Sep. 29, 2017, for PCT Application No. PCT/US2017/036417 filed Jun. 7, 2017 by KLA-Tencor Corporation, 3 pages.

* cited by examiner

SIMULTANEOUS MULTI-ANGLE SPECTROSCOPY

CROSS REFERENCE TO RELATED APPLICATION

The present application for patent claims priority under 35 U.S.C. § 119 from U.S. provisional patent application Ser. No. 62/348,870, entitled "Optics for Simultaneous Multi-angle Spectroscopy," filed Jun. 11, 2016, the subject matter of which is incorporated herein by reference in its entirety.

TECHNICAL FIELD

The described embodiments relate to metrology systems and methods, and more particularly to methods and systems for improved measurement of semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Measurements performed over multiple angles yield information with greater accuracy and precision. In one example, spectroscopic ellipsometry (SE) and spectroscopic reflectometry (SR) systems perform simultaneous measurements across a broad spectrum of illumination wavelengths. However, many existing SR and SE systems acquire measurement signals at one angle of incidence (AOI) at a time. This limits the throughput of such system when multiple AOIs are required to accurately characterize the sample.

In one example, a multi-angle SE instrument available from J. A. Woollam Co., Lincoln, Nebr. (USA), includes mechanisms for rotating the specimen under measurement, elements of the optical system, or both, to sequentially perform measurements at different AOI values. In another example, a multi-angle SE instrument available from KLA-Tencor Corp., Milpitas, Calif. (USA), employs a large numerical aperture (NA) optical system that captures all AOIs of interest simultaneously without moving the specimen or significant portions of the optical system.

In this example, the collection pupil contains the full range of angles reflected by the specimen. Depending on the NA of the system, the full range of angles could range from very small (e.g., collimated) to very large (e.g., greater than five degrees). In existing metrology system the reflected light over the full range of angles is not used to perform a measurement because measurement signal information associated with too many angles of incidence is integrated at the detector. The resulting loss of signal fidelity limits the effectivity of the measured signals. To mitigate this effect, the range of measured AOIs is limited to a few degrees about each nominal AOI that is spectrally measured.

In the multi-angle SE instrument available from KLA-Tencor, mechanical shutters are employed to sequentially measure spectra at one or more AOI sub-ranges. In this example, a specimen is illuminated with a large NA over the full wavelength range of interest and the reflected light is collected by the system optics. The collection pupil contains all the angles of interest, but mechanical shutters or beam blocks are employed to block all collected light except a selected range of AOIs from which light is collected. This selected range remains unblocked and is measured by the measurement sensor. In this approach the optics are maintained in a stationary configuration and AOI selection is achieved with mechanical shutters or masks. Sequential spectral measurements at different AOIs results in extended wafer exposure and overall measurement time. Furthermore, time-dependent effects that manifest on the wafer may be captured by the sequential measurements and negatively impact the measurement results.

In summary, ongoing reductions in feature size and increasing depths of structural features impose difficult requirements on optical metrology systems. Optical metrology systems must meet high precision and accuracy requirements for increasingly complex targets at high throughput to remain cost effective. In this context, speed of data collection and range of angles of incidence have emerged as important factors in the design of optical metrology systems. Thus, improved metrology systems and methods to overcome these limitations are desired.

SUMMARY

Methods and systems for performing simultaneous spectroscopic measurements of semiconductor structures over a broad range of angles of incidence, azimuth angles, or both, are presented herein. Spectra including two or more sub-ranges of angles of incidence, azimuth angles, or both, are simultaneously measured over different sensor areas at high throughput with the same alignment conditions. In this manner, machine errors, such as wavelength errors, are uniformly corrected across all measured wavelengths. Collected light is linearly dispersed across different photosensitive areas of one or more detectors according to wavelength for each subrange of AOIs, azimuth angles, or both. Each different photosensitive area is arranged on the one or more detectors to perform a separate spectroscopic measurement of each different range of AOIs, azimuth angles, or both. In this manner, a broad range of AOIs, azimuth angles, or both, are detected with high signal to noise ratio, simultaneously. These features, individually, or in combination, enable high throughput measurements of high aspect ratio structures (e.g., structures having depths of one micrometer or more) with high throughput, precision, and accuracy.

In one aspect, a pupil segmentation and dispersion device is configured to segment an image of the measurement pupil into two or more pupil segments and disperse the two or more pupil segments onto one or more detectors over spatially distinct sensor areas. Each pupil segment includes signal information associated with distinct sub-ranges of the multiple angles of incidence, multiple azimuth angles, or a combination thereof.

In this manner, two or more angular segments in the measurement pupil are spatially dispersed such that the measured spectra associated with each angular segment are spatially offset from one another. This allows simultaneous detection by multiple, different detectors, a multiple zone detector, or a combination thereof. In this approach the entire measurement pupil is imaged simultaneously; thus avoiding the limitations of sequential measurements.

In a further aspect, a fine focus sensor (FFS) is integrated into the detection subsystem to provide measurement input for focus error correction during measurement.

In another further aspect, the metrology systems described herein employ a multi-zone infrared detector that combines different sensitivity bands at different locations on a single detector package. The detector is configured to deliver a continuous spectrum of data at different sensitivities, depending on location of incidence. Collected light is linearly dispersed across the surface of the detector according to wavelength. Each different photosensitive area is arranged on the detector to sense a different range of incident wavelengths. In this manner, a broad range of infrared wavelengths are detected with high signal to noise ratio by a single detector.

In yet another further aspect, the pupil segmentation and dispersion device is dynamically reconfigurable within the metrology system. In some embodiments, each of the multiple grating segments are moveable in position, orientation, or both.

In yet another further aspect, the pupil segmentation and dispersion device is exchangeable within the metrology system. In this manner, an appropriate pupil segmentation and dispersion device may be selected and located in the collection optics path for a particular measurement application.

In yet another further aspect, the illumination field size is adjusted to optimize the resulting measurement accuracy and speed based on the nature of target under measurement.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for performing simultaneous spectroscopic measurements of semiconductor structures over a broad range of angles of incidence, azimuth angles, or both, are presented herein. Spectra including two or more subranges of angles of incidence, azimuth angles, or both, are simultaneously measured over different sensor areas at high throughput with the same alignment conditions. In this manner, machine errors, such as wavelength errors, are uniformly corrected across all measured wavelengths. Collected light is linearly dispersed across different photosensitive areas of one or more detectors according to wavelength for each subrange of AOIs, azimuth angles, or both. Each different photosensitive area is arranged on the one or more detectors to perform a separate spectroscopic measurement of each different range of AOIs, azimuth angles, or both. In this manner, a broad range of AOIs, azimuth angles, or both, are detected with high signal to noise ratio, simultaneously. These features, individually, or in combination, enable high throughput measurements of high aspect ratio structures (e.g., structures having depths of one micrometer or more) with high throughput, precision, and accuracy.

Figure 1:
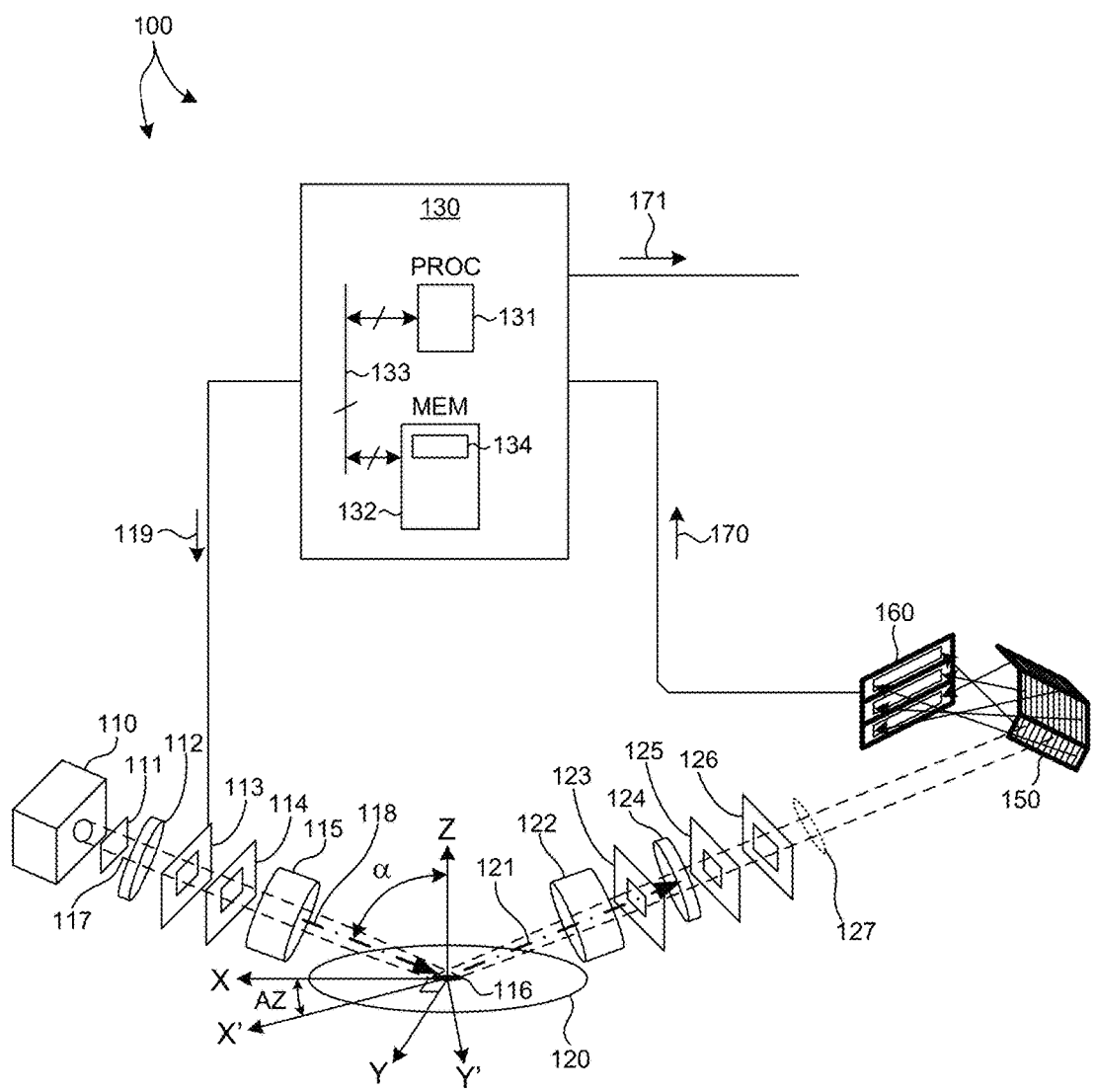
FIG. 1 depicts an exemplary, metrology system 100 for performing simultaneous spectroscopic measurements of semiconductor structures over a broad range of angles of incidence, azimuth angles, or both.

FIG. 1 depicts an exemplary, metrology system 100 for performing simultaneous spectroscopic measurements of semiconductor structures over a broad range of angles of incidence, azimuth angles, or both. In some examples, the one or more structures include at least one high aspect ratio (HAR) structure or at least one large lateral dimension structure. As depicted in FIG. 1, metrology system 100 is configured as a broadband spectroscopic ellipsometer. However, in general, metrology system 100 may be configured as a spectroscopic reflectometer, scatterometer, ellipsometer, or any combination thereof.

Metrology system 100 includes an illumination source 110 that generates a beam of illumination light 117 incidence on a wafer 120. In some embodiments, illumination source 110 is a broadband illumination source that emits illumination light in the ultraviolet, visible, and infrared spectra. In one embodiment, illumination source 110 is a laser sustained plasma (LSP) light source (a.k.a., laser driven plasma source). The pump laser of the LSP light source may be continuous wave or pulsed. A laser-driven plasma source can produce significantly more photons than a Xenon lamp across the entire wavelength range from 150 nanometers to 2000 nanometers. Illumination source 110 can be a single light source or a combination of a plurality of broadband or discrete wavelength light sources. The light generated by illumination source 110 includes a continuous spectrum or parts of a continuous spectrum, from ultraviolet to infrared (e.g., vacuum ultraviolet to mid infrared). In general, illumination light source 110 may include a super continuum laser source, an infrared helium-neon laser source, an arc lamp, or any other suitable light source.

In a further aspect, the amount of illumination light is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 120 nanometers and 3,000 nanometers. In some embodiments, broadband illumination light including wavelengths beyond 3,000 nanometers may be employed.

As depicted in FIG. 1, metrology system 100 includes an illumination subsystem configured to direct illumination light 117 to one or more structures formed on the wafer 120. The illumination subsystem is shown to include light source 110, one or more optical filters 111, polarizing component 112, field stop 113, aperture stop 114, and illumination optics 115. The one or more optical filters 111 are used to control light level, spectral output, or both, from the illumination subsystem. In some examples, one or more multi-zone filters are employed as optical filters 111. Polarizing component 112 generates the desired polarization state exiting the illumination subsystem. In some embodiments, the polarizing component is a polarizer, a compensator, or both, and may include any suitable commercially available polarizing component. The polarizing component can be fixed, rotatable to different fixed positions, or continuously rotating. Although the illumination subsystem depicted in FIG. 1 includes one polarizing component, the illumination subsystem may include more than one polarizing component. Field stop 113 controls the field of view (FOV) of the illumination subsystem and may include any suitable commercially available field stop. Aperture stop 114 controls the numerical aperture (NA) of the illumination subsystem and may include any suitable commercially available aperture stop. Light from illumination source 110 is directed through illumination optics 115 to be focused on one or more structures (not shown in FIG. 1) on wafer 120. The illumination subsystem may include any type and arrangement of optical filter(s) 111, polarizing component 112, field stop 113, aperture stop 114, and illumination optics 115 known in the art of spectroscopic ellipsometry, reflectometry, and scatterometry.

As depicted, in FIG. 1, the beam of illumination light 117 passes through optical filter(s) 111, polarizing component 112, field stop 113, aperture stop 114, and illumination optics 115 as the beam propagates from the illumination source 110 to wafer 120. Beam 117 illuminates a portion of wafer 120 over a measurement spot 116.

In some examples, the beam size of the amount of illumination light 117 projected onto the surface of wafer 120 is smaller than a size of a measurement target that is measured on the surface of the specimen. Exemplary beam shaping techniques are described in detail in U.S. Patent Application Publication No. 2013/0114085 by Wang et al., the contents of which are incorporated herein by reference in their entirety.

Metrology system 100 also includes a collection optics subsystem configured to collect light generated by the interaction between the one or more structures and the incident illumination beam 117. A beam of collected light 127 is collected from measurement spot 116 by collection optics 122. Collected light 127 passes through collection aperture stop 123, polarizing element 124, and field stop 125 of the collection optics subsystem.

Collection optics 122 includes any suitable optical elements to collect light from the one or more structures formed on wafer 120. Collection aperture stop 123 controls the NA of the collection optics subsystem. Polarizing element 124 analyzes the desired polarization state. The polarizing element 124 is a polarizer or a compensator. The polarizing element 124 can be fixed, rotatable to different fixed positions, or continuously rotating. Although the collection subsystem depicted in FIG. 1 includes one polarizing element, the collection subsystem may include more than one polarizing element. Collection field stop 125 controls the FOV of the collection subsystem. The collection subsystem takes light from wafer 120 and directs the light through collection optics 122, and polarizing element 124 to be focused on collection field stop 125. In some embodiments, collection field stop 125 is used as a spectrometer slit for the spectrometers of the detection subsystem. However, collection field stop 125 may be located at or near a spectrometer slit 126 of the spectrometers of the detection subsystem.

The collection subsystem may include any type and arrangement of collection optics 122, aperture stop 123, polarizing element 124, and field stop 125 known in the art of spectroscopic ellipsometry, reflectometry, and scatterometry.

In the embodiment depicted in FIG. 1, the collection optics subsystem directs light to one or more spectrometers of the detection subsystem. The detection subsystem generates output responsive to light collected from the one or more structures illuminated by the illumination subsystem.

As depicted in FIG. 1, the Z-axis is oriented normal to the surface of wafer 120. The X and Y axes are coplanar with the surface of wafer 120, and thus perpendicular to the Z-axis. Similarly, the X' and Y' axes are coplanar with the surface of wafer 120, and thus perpendicular to the Z-axis. The X' and Y' axes are rotated with respect to the X and Y axes by an azimuth angle, AZ. The azimuth angle specifies the orientation of light delivery to wafer 120 about the Z-axis. The chief ray 118 of the beam of illumination light 117 and the chief ray 121 of the beam of collected light 127 define a plane of incidence. The X'-axis is aligned with the plane of incidence and the Y'-axis is orthogonal to the plane of incidence. In this manner, the plane of incidence lies in the X'Z plane. The beam of illumination light 117 is incident on the surface of wafer 120 at an angle of incidence, $\alpha$, with respect to the Z-axis and lies within the plane of incidence.

In one aspect, a pupil segmentation and dispersion device is configured to segment an image of the measurement pupil into two or more pupil segments and disperse the two or more pupil segments onto one or more detectors over spatially distinct sensor areas. Each pupil segment includes signal information associated with distinct sub-ranges of the multiple angles of incidence, multiple azimuth angles, or a combination thereof. In some embodiments, the pupil segmentation and dispersion device is located at or near an aperture stop of the metrology system or at or near a conjugate of an aperture stop of the metrology system.

In this manner, two or more angular segments in the measurement pupil are spatially dispersed such that the measured spectra associated with each angular segment are spatially offset from one another. This allows simultaneous detection by multiple, different detectors, a multiple zone detector, or a combination thereof. In this approach the entire measurement pupil is imaged simultaneously; thus avoiding the limitations of sequential measurements.

The measurement pupil (i.e., collection pupil) is typically located at or near the collection lens 122. The measurement pupil includes the full range of angles reflected by the wafer 120. The full range of angles depends on the NA of the optical design, but it could vary from very small (e.g., collimated) to very large (e.g., greater than five degrees). If all of the reflected light over a full range of angles is aggregated in one measured spectra, the measured signal typically suffers from loss of fidelity because too many angles are integrated in the measurement signal. Previously, it has been common practice to limit the angular range of a particular measured spectra to a few degrees around a nominal angle of incidence under consideration during a particular measurement.

As described herein, an image of the measurement pupil is separated in angle and wavelength to simultaneously generate multiple spectra, each segment corresponding to a different nominal angle and sub-range of angles about the nominal angle. The generated spectra are spatially separated from one another and separately detected by one or more detectors (e.g., separate detectors, a multi-zone detector, or a combination thereof).

In the embodiment depicted in FIG. 1, collected light 127 passes through spectrometer slit 126 and is incident on pupil segmentation and dispersion device 150. In the embodiment depicted in FIG. 1, the pupil segmentation and dispersion device includes multiple reflective gratings. Each reflective grating is set at a different angle with respect to one another. Light dispersed from each grating toward detector subsystem 160 is spatially separated at the surfaces of detector subsystem 160.

Figure 2:
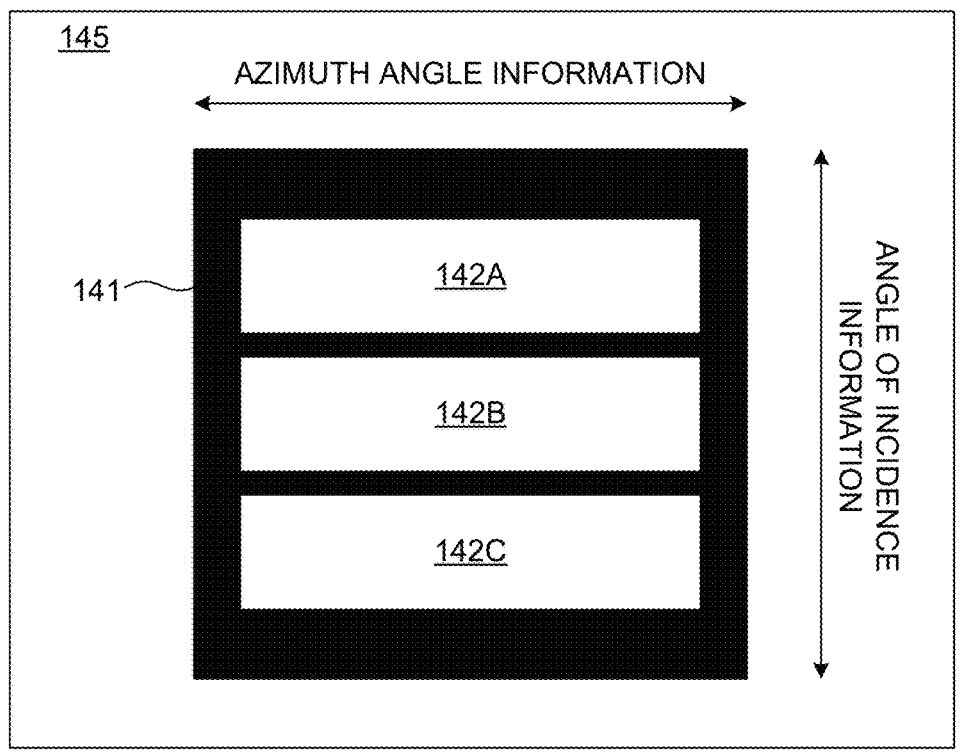
FIG. 2 depicts a mask 141 in the plane of a measurement pupil image 145 of metrology system 100.

FIG. 2 depicts a measurement pupil image 145 of metrology system 100. As depicted in FIG. 2, the measurement pupil image 145 includes angle of incidence information dispersed across one direction of the image and azimuth angle information across another direction of the image. FIG. 2 also depicts a mask 141 in the plane of the image of the measurement pupil 145. As depicted in FIG. 2, mask 141 obscures portions of the image, leaving three pupil segments 142A-C available for transmission. Each of these pupil segments includes the same azimuth angle information, but different angle of incidence information. In this manner, mask 141 subdivides the image of the measurement pupil 145 into different segments, each associated with different ranges of angles of incidence.

Figure 3:
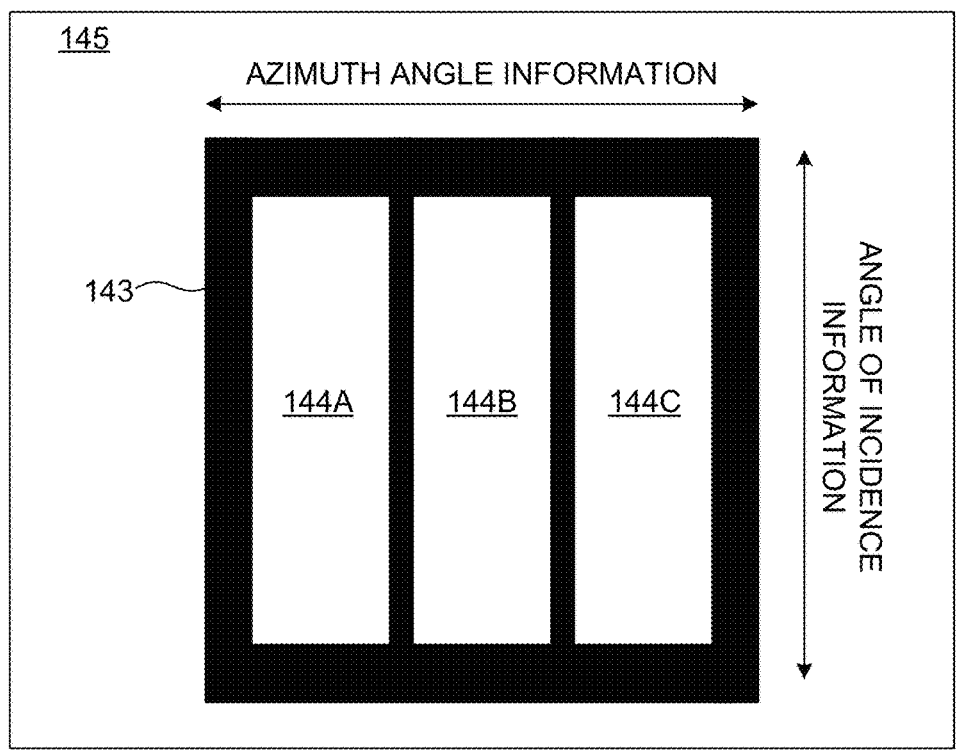
FIG. 3 depicts a mask 143 in the plane of a measurement pupil image 145 of metrology system 100.

FIG. 3 depicts another illustration of measurement pupil image 145 of metrology system 100. As depicted in FIG. 3, the measurement pupil image 145 includes angle of incidence information dispersed across one direction of the image and azimuth angle information across another direction of the image. FIG. 3 depicts a mask 143 in the plane of the image of the measurement pupil 145. As depicted in FIG. 3, mask 143 obscures portions of the image, leaving three pupil segments 144A-C available for transmission. Each of these pupil segments includes the same AOI information, but different azimuth angle information. In this manner, mask 143 subdivides the image of the measurement pupil 145 into different segments, each associated with different ranges of azimuth angle.

The depicted images of measurement pupil 145 are segmented into three segments. However, in general, any number of different segments may be contemplated within the scope of this patent document. Furthermore, FIGS. 2 and 3 illustrate segmentation examples along AOI and azimuth angle directions. However, in general, segmentation of the measurement pupil along any direction in the image plane of the measurement pupil may be contemplated within the scope of this patent document. In this manner, each segment may include different AOI and Azimuth angle information. In one example, both masks 141 and 143 may be employed in the image plane to subdivide the measurement pupil into nine different segments, each having different AOI and azimuth angle information. In another example, mask 141 or mask 143 may be rotated within the image plane to capture different swathes of AOI and Azimuth angle information.

FIGS. 2 and 3 depict illustrations of a mask located in an image plane of the measurement pupil of metrology system 100 before the pupil segmentation and dispersion device. The mask defines segments of angular information for separate and simultaneous measurement. Such a mask may be advantageous to enable precise subdivisions of the measurement pupil before incidence on the pupil segmentation and dispersion device. However, in general, the pupil segmentation and dispersion techniques described herein do not require a mask located in an image plane of the measurement pupil. Where a mask is not employed, the segmentation and dispersion device will segment the measurement pupil by directing different portions of the incoming beam to different areas of the detector subsystem based the location of incidence of the collected beam onto the segmentation and dispersion device. As such the pupil segmentation and dispersion device may be arranged in any suitable manner to segment the measurement pupil in the desired manner.

Figure 4:
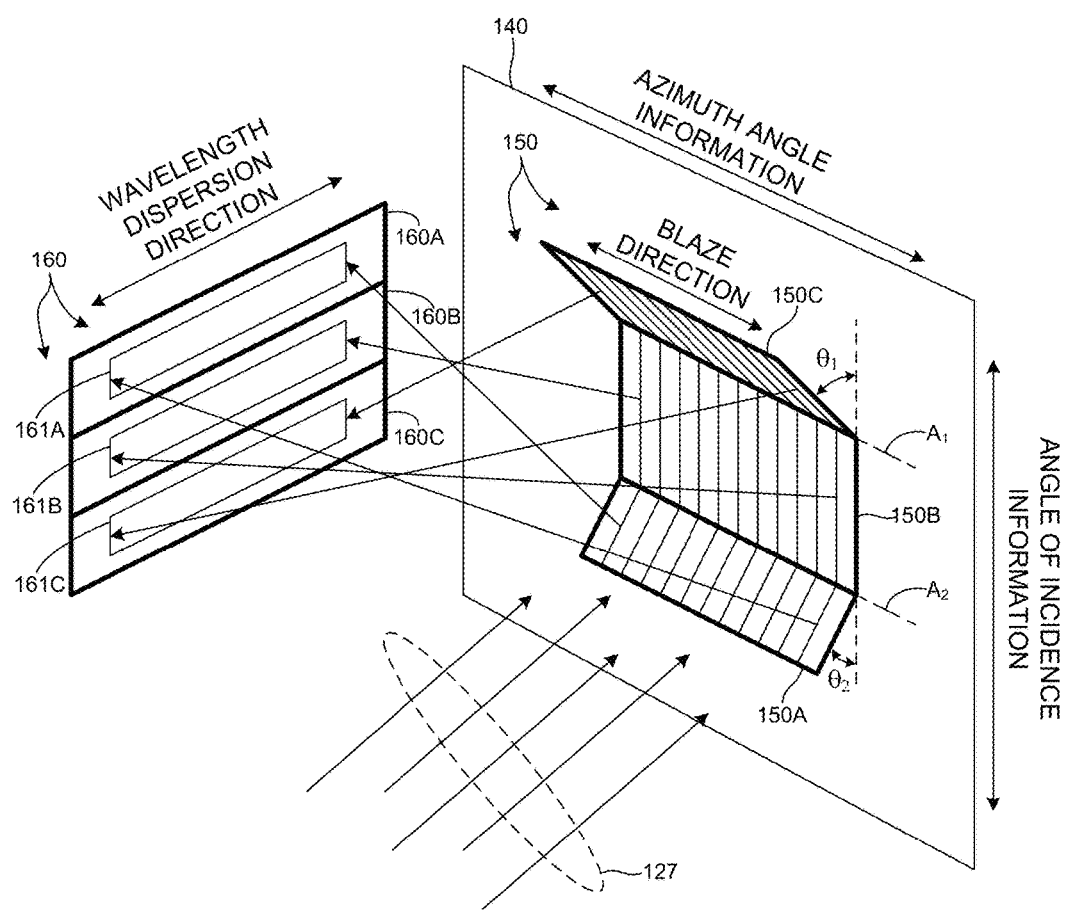
FIG. 4 depicts another illustration of the pupil segmentation and dispersion device 150 and detector subsystem 160 depicted in FIG. 1.

FIG. 4 depicts another illustration of the pupil segmentation and dispersion device 150 and detector subsystem 160 depicted in FIG. 1. As depicted in FIG. 4, pupil segmentation and dispersion device 150 is located at or near an image plane 140 of the measurement pupil of metrology system 100. At image plane 140, collection beam 127 includes azimuth angle information dispersed in one direction and angle of incidence information dispersed in another direction. Pupil segmentation and dispersion device 150 includes three reflective grating segments 150A-C. As depicted in FIG. 4, the portion of collected light 127 incident on each segment includes the same azimuth angle information, but different angle of incidence information. In this embodiment, the three reflective grating segments correspond to the three pupil image segments illustrated in FIG. 2. By locating the pupil segmentation and dispersion device at or near an image plane of the measurement pupil, pupil segments having different angular information are spatially distinguished and separately dispersed onto different sensor areas of a detector subsystem.

In the embodiment depicted in FIG. 4, each reflective grating segment is oriented at a different angle with respect to one another. For example, reflective grating segment 150B is oriented in the image plane 140, reflective grating segment 150A is orientated at an angle θ2, with respect to the image plane 140, and reflective grating segment 150C is orientated at an angle θ1, with respect to image plane 140. As illustrated in FIG. 4, the different orientations cause the each segment to disperse the incoming light in a different direction.

In the embodiment depicted in FIG. 4, the reflective grating segment 150C is tilted by angle θ1 about axis A1 that lies within image plane 140 and extends in a direction parallel to the blaze direction of the grating structures of reflective grating segments 150A-C. Similarly, the reflective grating segment 150A is tilted by angle θ2 about axis A2 that lies within image plane 140 and extends in a direction parallel to the blaze direction of the grating structures of reflective grating segments 150A-C. In this configuration, measured spectrum 161A dispersed by reflective grating segment 150A is incident on detector 160A, measured spectrum 161B dispersed by reflective grating segment 150B is incident on detector 160B, and measured spectrum 161C dispersed by reflective grating segment 150C is incident on detector 160C. As depicted in FIG. 4, detector subsystem 160 includes three detectors 160A-C, each disposed on top of one another in a direction orthogonal to the direction of wavelength dispersion. The magnitude of angles, $\theta 1$ and $\theta 2$ determines the magnitude of the spatial shift at the detectors.

The diffractive gratings of pupil segmentation and dispersion device 150 linearly disperse first order diffracted light according to wavelength along one dimension of each respective two dimensional detector (i.e., the wavelength dispersion direction noted in FIG. 4 for each respective detector). Each diffractive grating segment causes a spatial separation between two different wavelengths of light projected onto the surface of each corresponding detector along the direction of wavelength dispersion.

In one example, the detectors of detector subsystem 160 are charge coupled devices (CCD) sensitive to ultraviolet and visible light (e.g., light having wavelengths between 190 nanometers and 860 nanometers). In other examples, one or more of the detectors of detector subsystem 160 is a photo detector array (PDA) sensitive to infrared light (e.g., light having wavelengths between 950 nanometers and 2500 nanometers). However, in general, other two dimensional detector technologies may be contemplated (e.g., a position sensitive detector (PSD), an infrared detector, a photovoltaic detector, etc.). Each detector converts the incident light into electrical signals indicative of the spectral intensity of the incident light. In general, detector subsystem 160 generates output signals 170 indicative of light simultaneously detected on each detector of the detector subsystem 160.

As depicted in FIG. 1, the detection subsystem is arranged such that the collected light propagates to all detectors of metrology system 100, simultaneously. Metrology system 100 also includes computing system 130 configured to receive detected signals 170 and determines an estimate of a value of a parameter of interest 171 of the measured structure(s) based on the measured signals. By simultaneously collecting spectra associated with different angular data, measurement times are reduced and all spectra are measured with the same alignment conditions. This allows wavelength errors to be corrected more easily because a common correction can be applied to all spectral data sets.

Figure 5:
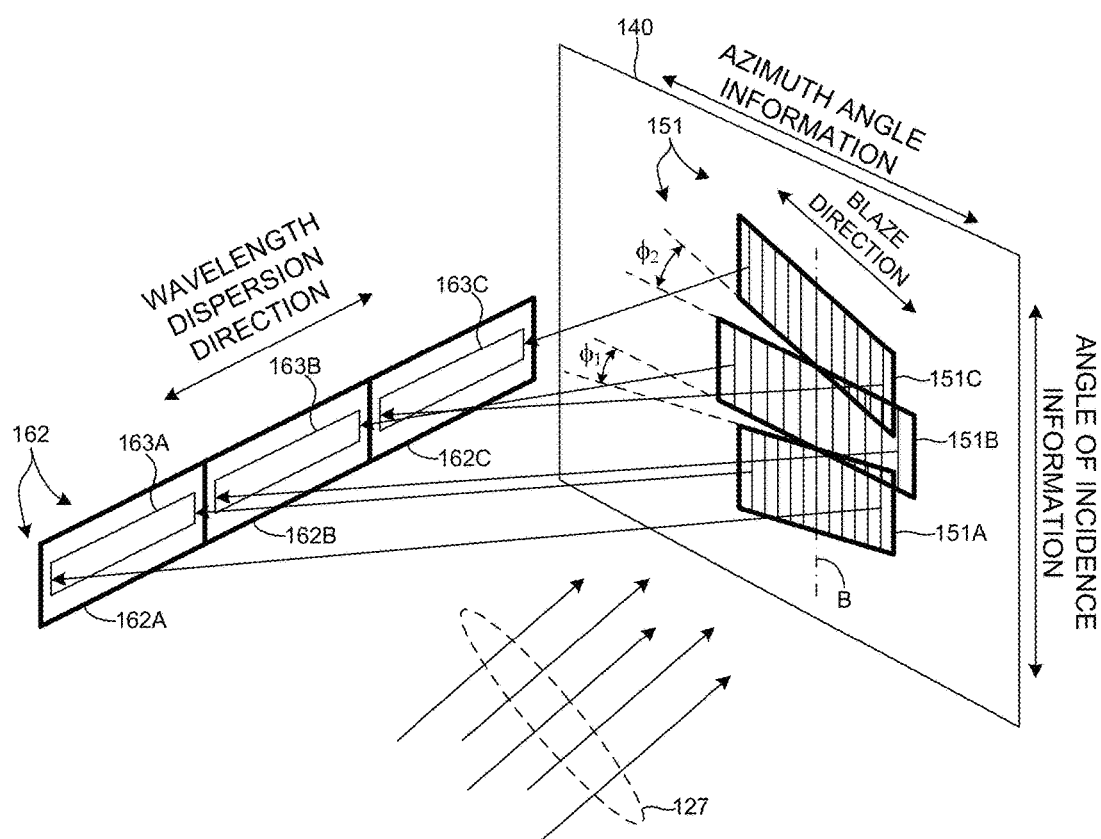
FIG. 5 depicts an illustration of a pupil segmentation and dispersion device 151 and detector subsystem 162 in another embodiment.

FIG. 5 depicts an illustration of a pupil segmentation and dispersion device 151 and detector subsystem 162 in another embodiment. As depicted in FIG. 5, pupil segmentation and dispersion device 151 is located at or near an image plane 140 of the measurement pupil of metrology system 100. In this embodiment, pupil segmentation and dispersion device 151 includes three reflective grating segments 151A-C. As depicted in FIG. 5, the portion of collected light 127 incident on each segment includes the same azimuth angle information, but different angle of incidence information. In this embodiment, the three reflective grating segments correspond to the three pupil image segments illustrated in FIG. 2.

In the embodiment depicted in FIG. 5, each reflective grating segment is oriented at a different angle with respect to one another. For example, reflective grating segment 151B is oriented in the image plane 140, reflective grating segment 151A is orientated at an angle $\theta 1$, with respect to the image plane 140, and reflective grating segment 151C is orientated at an angle $\theta 2$, with respect to image plane 140. As illustrated in FIG. 5, the different orientations cause each segment to disperse the incoming light in a different direction.

In the embodiment depicted in FIG. 5, the reflective grating segment 151C is tilted by angle $\theta 2$ about axis B that lies within image plane 140 and extends in a direction perpendicular to the blaze direction of the grating structures of reflective grating segments 151A-C. Similarly, the reflective grating segment 151A is tilted by angle $\theta 1$ about axis B. In this configuration, measured spectrum 163A dispersed by reflective grating segment 151A is incident on detector 162A, measured spectrum 163B dispersed by reflective grating segment 151B is incident on detector 162B, and measured spectrum 163C dispersed by reflective grating segment 151C is incident on detector 162C. As depicted in FIG. 5, detector subsystem 162 includes three detectors 162A-C, each disposed adjacent to one another, parallel to the direction of wavelength dispersion. The magnitude of angles, $\theta 1$ and $\theta 2$ determines the magnitude of the spatial shift at the detectors.

Figure 6:
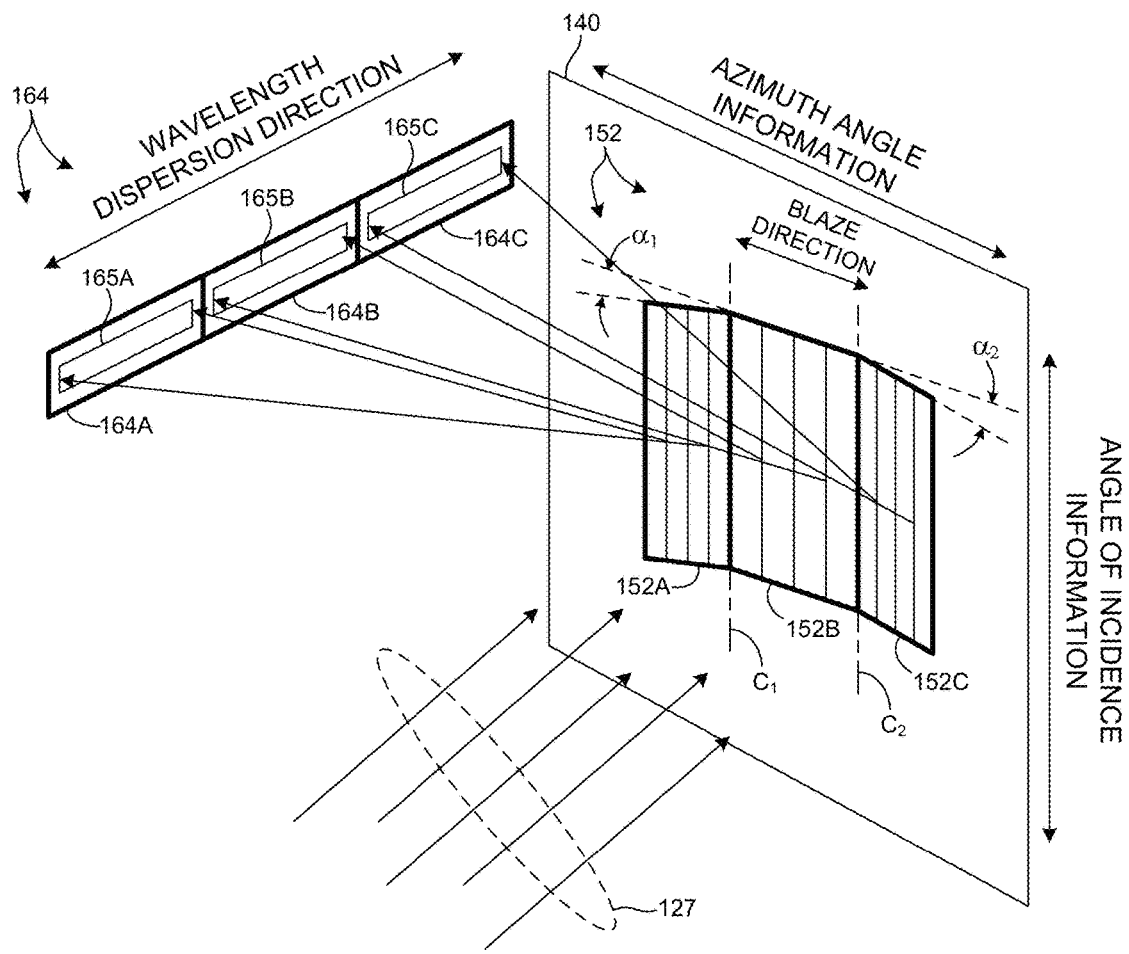
FIG. 6 depicts an illustration of a pupil segmentation and dispersion device 152 and detector subsystem 164 in yet another embodiment.

FIG. 6 depicts an illustration of a pupil segmentation and dispersion device 152 and detector subsystem 164 in another embodiment. As depicted in FIG. 6, pupil segmentation and dispersion device 152 is located at or near an image plane 140 of the measurement pupil of metrology system 100. In this embodiment, pupil segmentation and dispersion device 152 includes three reflective grating segments 152A-C. As depicted in FIG. 6, the portion of collected light 127 incident on each segment includes the same angle of incidence information, but different azimuth angle information. In this embodiment, the three reflective grating segments correspond to the three pupil image segments illustrated in FIG. 3.

In the embodiment depicted in FIG. 6, each reflective grating segment is oriented at a different angle with respect to one another. For example, reflective grating segment 152B is oriented in the image plane 140, reflective grating segment 152A is orientated at an angle $\alpha 1$, with respect to the image plane 140, and reflective grating segment 152C is orientated at an angle $\alpha 2$, with respect to image plane 140. As illustrated in FIG. 6, the different orientations cause each segment to disperse the incoming light in a different direction.

In the embodiment depicted in FIG. 6, the reflective grating segment 152C is tilted by angle $\alpha 2$ about axis C2 that lies within image plane 140 and extends in a direction parallel to the blaze direction of the grating structures of reflective grating segments 152A-C. Similarly, the reflective grating segment 152A is tilted by angle $\alpha 1$ about axis C1. In this configuration, measured spectrum 165A dispersed by reflective grating segment 152A is incident on detector 164A, measured spectrum 165B dispersed by reflective grating segment 152B is incident on detector 164B, and measured spectrum 165C dispersed by reflective grating segment 152C is incident on detector 164C. As depicted in FIG. 6, detector subsystem 164 includes three detectors 164A-C, each disposed adjacent to one another, parallel to the direction of wavelength dispersion. The magnitude of angles, $\alpha 1$ and $\alpha 2$ determines the magnitude of the spatial shift at the detectors.

Figure 7:
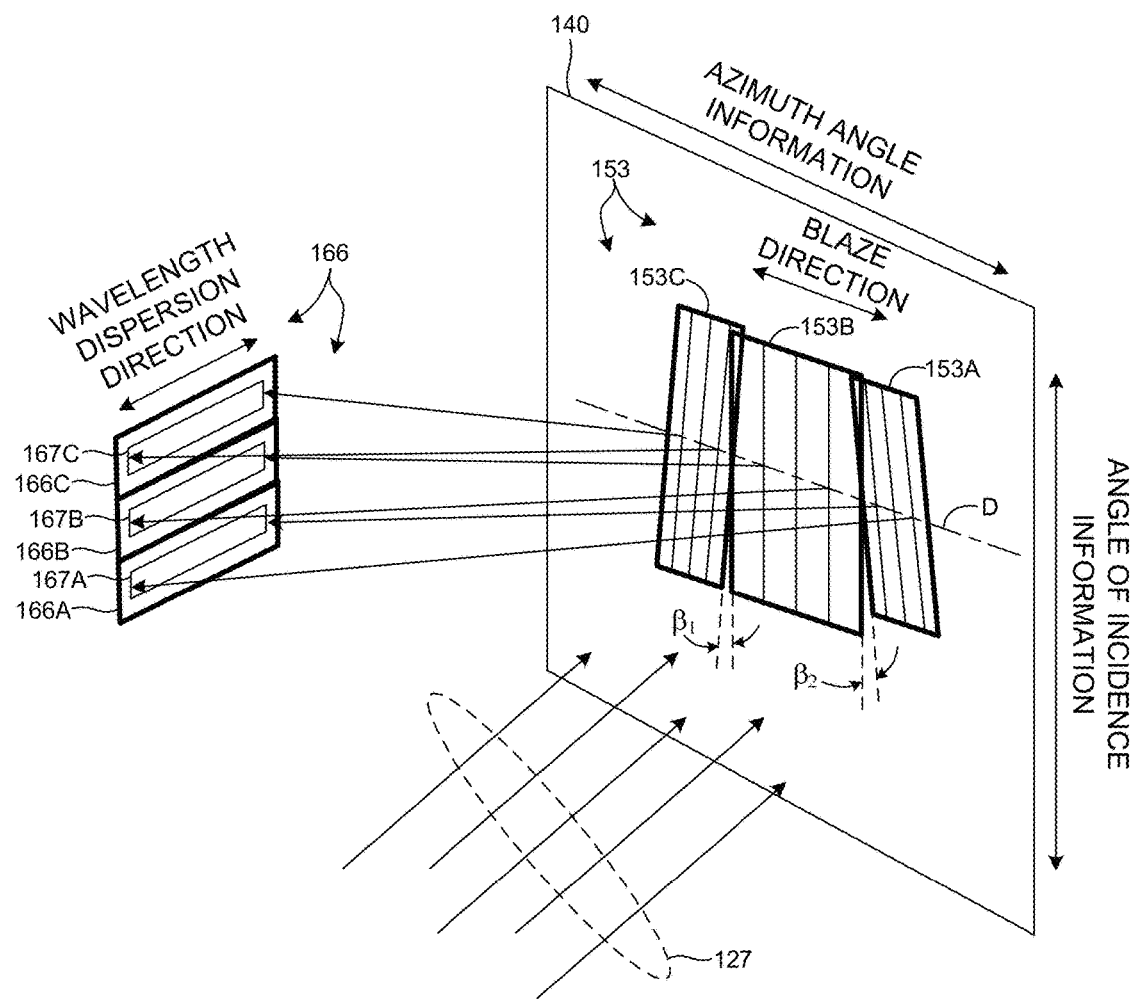
FIG. 7 depicts an illustration of a pupil segmentation and dispersion device 153 and detector subsystem 166 in another embodiment.

FIG. 7 depicts an illustration of a pupil segmentation and dispersion device 153 and detector subsystem 166 in another embodiment. As depicted in FIG. 7, pupil segmentation and dispersion device 153 is located at or near an image plane 140 of the measurement pupil of metrology system 100. In this embodiment, pupil segmentation and dispersion device 153 includes three reflective grating segments 153A-C. As depicted in FIG. 7, the portion of collected light 127 incident on each segment includes the same angle of incidence information, but different azimuth angle information. In this embodiment, the three reflective grating segments correspond to the three pupil image segments illustrated in FIG. 3.

In the embodiment depicted in FIG. 7, each reflective grating segment is oriented at a different angle with respect to one another. For example, reflective grating segment 153B is oriented in the image plane 140, reflective grating segment 153A is orientated at an angle β2, with respect to the image plane 140, and reflective grating segment 153C is orientated at an angle β1, with respect to image plane 140. As illustrated in FIG. 7, the different orientations cause each segment to disperse the incoming light in a different direction.

In the embodiment depicted in FIG. 7, the reflective grating segment 153C is tilted by angle β1 about axis D that lies within image plane 140 and extends in a direction perpendicular to the blaze direction of the grating structures of reflective grating segments 153A-C. Similarly, the reflective grating segment 153A is tilted by angle β1 about axis D. In this configuration, measured spectrum 167A dispersed by reflective grating segment 153A is incident on detector 166A, measured spectrum 167B dispersed by reflective grating segment 153B is incident on detector 166B, and measured spectrum 167C dispersed by reflective grating segment 153C is incident on detector 166C. As depicted in FIG. 7, detector subsystem 166 includes three detectors 166A-C, each disposed adjacent to one another, perpendicular to the direction of wavelength dispersion. The magnitude of angles, β1 and β2 determines the magnitude of the spatial shift at the detectors.

In the embodiments described with reference to FIGS. 4-7, the detector elements of each respective detector subsystem are separate detectors arranged in a stacked arrangement (e.g., on top of one another or end to end). However, in general, the detector elements may be arranged in any suitable manner to receive dispersed light from each respective pupil segment generated by the pupil segmentation and dispersion device. In addition, in some embodiments multiple detector elements are configured to receive light from a particular pupil segment over different wavelength bands. In one embodiment, a measured spectrum dispersed from a particular pupil segment is detected by a charge coupled device (CCD) sensor in a wavelength band that includes ultraviolet wavelengths and by a photo detector array (PDA) in a wavelength band that includes infrared wavelengths. In general, any suitable combination of detecting elements may be employed to detect a measured spectrum dispersed from any particular pupil segment generated by the pupil segmentation and dispersion device.

In some embodiments, a detector subsystem includes a multi-zone infrared detector that combines different sensitivity bands at different locations on a single detector package. The detector is configured to deliver a continuous spectrum of data at different sensitivities, depending on location of incidence.

Figure 9:
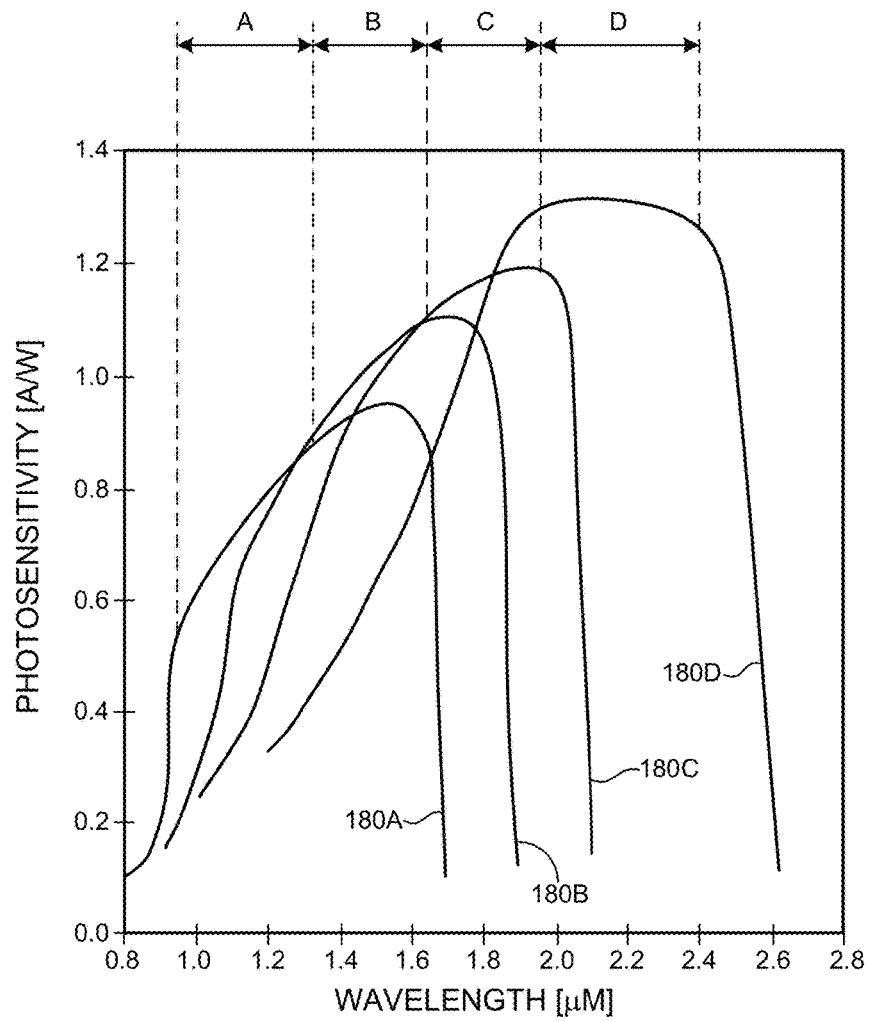
FIG. 9 illustrates typical photosensitivity curves of four available Indium Gallium Arsenide (InGaAs) sensors.

FIG. 9 illustrates typical photosensitivity curves of available Indium Gallium Arsenide (InGaAs) sensors. As depicted in FIG. 9, no single sensor of the available InGaAs sensors is capable of providing adequate photosensitivity across a wavelength band from 1 micrometer to 2.5 micrometers. Thus, individually, the available sensors are only capable of sensing over a narrow waveband.

In one aspect, multiple sensor chips, each sensitive in a different waveband are combined into a single detector package. In turn, this multi-zone detector is implemented in the metrology systems described herein.

Figure 8:
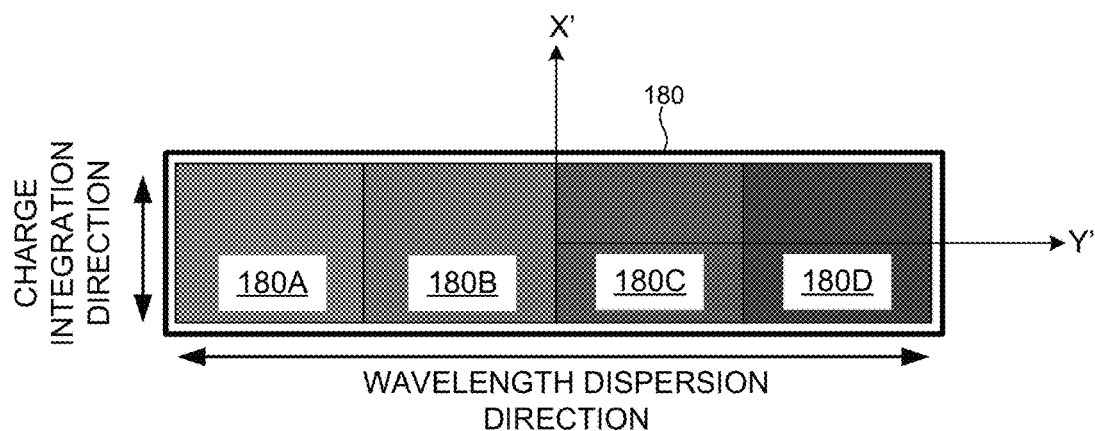
FIG. 8 depicts an illustration of a multi-zone infrared detector 180.

FIG. 8 depicts four sensor chips 180A-D derived from four different wavebands to make a multi-zone infrared detector 180. The four sensor chips include different material compositions that each exhibit different photosensitivity characteristics. As depicted in FIG. 9, sensor chip 180A exhibits high sensitivity over a waveband, A, sensor chip 180B exhibits high sensitivity over a waveband, B, sensor chip 180C exhibits high sensitivity over a waveband, C, and sensor chip 180D exhibits high sensitivity over a waveband, D. A metrology system incorporating detector 180 is configured to disperse wavelengths within waveband A onto sensor chip 180A, disperse wavelengths within waveband B onto sensor chip 180B, disperse wavelengths within waveband C onto sensor chip 180C, and disperse wavelengths within waveband D onto sensor chip 180D. In this manner, high photosensitivity (i.e., high SNR) is achieved over the aggregate waveband that includes wavebands A-D from a single detector.

In some examples, a multi-zone detector includes InGaAs sensors with sensitivity to different spectral regions assembled in a single sensor package to produce a single, contiguous spectrum covering wavelengths from 750 nanometers to 3,000 nanometers, or beyond.

In general, any number of individual sensors may be assembled along the direction of wavelength dispersion of the multi-zone detector such that a contiguous spectrum maybe derived from the detector. However, typically, two to four individual sensors are employed in a multi-zone detector, such as detector 180.

The embodiments of a pupil segmentation and dispersion device depicted in FIGS. 4-7 are provided by way of non-limiting example. Although, the illustrated embodiments include three different reflective grating segments, in general, any number of different segments greater than one may be contemplated within the scope of this patent document. In addition, the orientation angle between each grating element and the measurement pupil image plane may be the same for all grating elements, or different. In this manner, the tilt angles are configured to achieve the desired separation among simultaneously measured spectra. In some embodiments, the pupil segments are tilted with respect to an axis parallel to the blaze direction and with respect to an axis perpendicular to the blaze direction.

Furthermore, the shape and arrangement of different segments is not limited by the illustrations provided in FIGS. 4-7. Any number of different shapes and arrangement of segments may be contemplated within the scope of this patent document. In some examples, the segments are arranged such that each segment includes different AOI and Azimuth angle information. In one example, a two dimensional array of grating segments are arranged across the measurement pupil. In another example, a one dimensional or two dimensional array of grating segments is oriented at an oblique angle with respect to a direction of dispersion of angle of incidence or azimuth angle in the measurement pupil. In one example, a one dimensional array of grating segments is oriented diagonally through the measurement pupil to mix angular information in a desired manner.

Although, the illustrated embodiments include reflective grating segments, other dispersion elements may be contemplated within the scope of this patent document. In some embodiments, transmissive grating elements are employed to disperse incident light. In another example, segmented prism optics are employed to disperse incident light. In some embodiments, the orientation of the grating or prism elements determines the direction of dispersion of light from each pupil segment. However, in some other embodiments, mirror elements are employed to direct light dispersed by the grating or prism elements to different detector elements.

In some embodiments, each grating segment has the same period and reflection function. However, in some other embodiments, one or more of the grating segments include different grating periods and reflection functions. In this manner, different dispersion characteristics are generated for different pupil segments. This approach may be advantageous to optimize signal levels or sensor designs to meet measurement system requirements.

In some embodiments, a sequential grating arrangement is employed to disperse different wavebands of each pupil segment. In one embodiment, a reflective grating segment disperses ultraviolet light at the +1/−1 diffraction order and reflects infrared light at the zeroth diffraction order. The reflected infrared light is subsequently dispersed by a subsequent grating element.

In a further aspect, the pupil segmentation and dispersion device is dynamically reconfigurable within metrology system 100. In some embodiments, each of the multiple grating segments are moveable in position, orientation, or both. The position, orientation, or both, of each of the grating segments is controlled by computing system 130. Computing system 130 communicates control signals to a dynamically reconfigureable pupil segmentation and dispersion device. In response, the pupil segmentation and dispersion device adjusts a position, orientation, or both, of one or more of the pupil segments to select the desired angular information over the measurement pupil and disperse the corresponding spectra to the appropriate detector elements.

In some embodiments, a dynamically reconfigurable pupil segmentation and dispersion device includes a microelectromechanical (MEMS) array of reflective or transmissive grating elements configured to disperse light including different angular information to different detector elements.

In another further aspect, the pupil segmentation and dispersion device is exchangeable within metrology system 100. In this manner, an appropriate pupil segmentation and dispersion device may be selected and located in the collection optics path for a particular measurement application.

In the embodiment depicted in FIG. 1, the pupil segmentation and dispersion device includes multiple reflective grating segments. However, in addition to pupil segmentation, the pupil segmentation and dispersion device may also be configured to subdivide the incident light into different wavelength bands, propagate the different wavelength bands in different directions, and disperse the light of one of the wavelength bands onto one or more detectors in any suitable manner. In some examples, a beamsplitting element is employed to subdivide the collection beam 127 into different wavelength bands and separate reflective grating structures are employed to segment the measurement pupil in each wavelength band.

In the embodiments depicted in FIGS. 4-7, a reflective grating is employed because it exhibits high diffraction efficiency into the +/−1 orders. By employing a reflective grating, losses inherent to beam splitting elements (such as a dichroic beam splitting element) are avoided.

In a further aspect, a fine focus sensor (FFS) is integrated into the detection subsystem to provide measurement input for focus error correction during measurement. In some embodiments, light diffracted from one or more of the reflective grating segments at the zeroth diffraction order is directed to a fine focus sensor. In some embodiments, the FFS is a photo diode array. Output generated by the FFS (not shown) is communicated to computing system 130. Computing system 130 determines changes in focus position (z-position) of wafer 120 based on the output of the FFS. Any desired changes in focus position of wafer 120 are communicated to a wafer positioning system (not shown) that adjusts the z-position of wafer 120, accordingly.

In another further aspect, the illumination field stop size is selected to optimize the resulting measurement accuracy and speed based on the nature of target under measurement.

In another further aspect, the illumination field stop size is adjusted to optimize the resulting measurement accuracy and speed based on the nature of target under measurement.

In some examples, the illumination field stop size is adjusted to achieve desired spectral resolution. In some examples, the illumination field stop size is adjusted to increase light throughput and achieve a shortened measurement time.

In the embodiment depicted in FIG. 1, computing system 130 is configured to receive signals 170 indicative of the spectral response detected by detector subsystem 160. Computing system 130 is further configured to determine control signals 119 that are communicated to programmable illumination field stop 113. Programmable illumination field stop 113 receives control signals 119 and adjusts the size of the illumination aperture to achieve the desired illumination field size.

In some examples, the illumination field stop is adjusted to optimize measurement accuracy and speed as described hereinbefore. In another example, the illumination field stop is adjusted to prevent image clipping by the spectrometer slit and corresponding degradation of measurement results. In this manner, the illumination field size is adjusted such that the image of the measurement target underfills the spectrometer slit. In one example, the illumination field stop is adjusted such that the projection of the polarizer slit of the illumination optics underfills the spectrometer slit of the metrology system.

Figure 11:
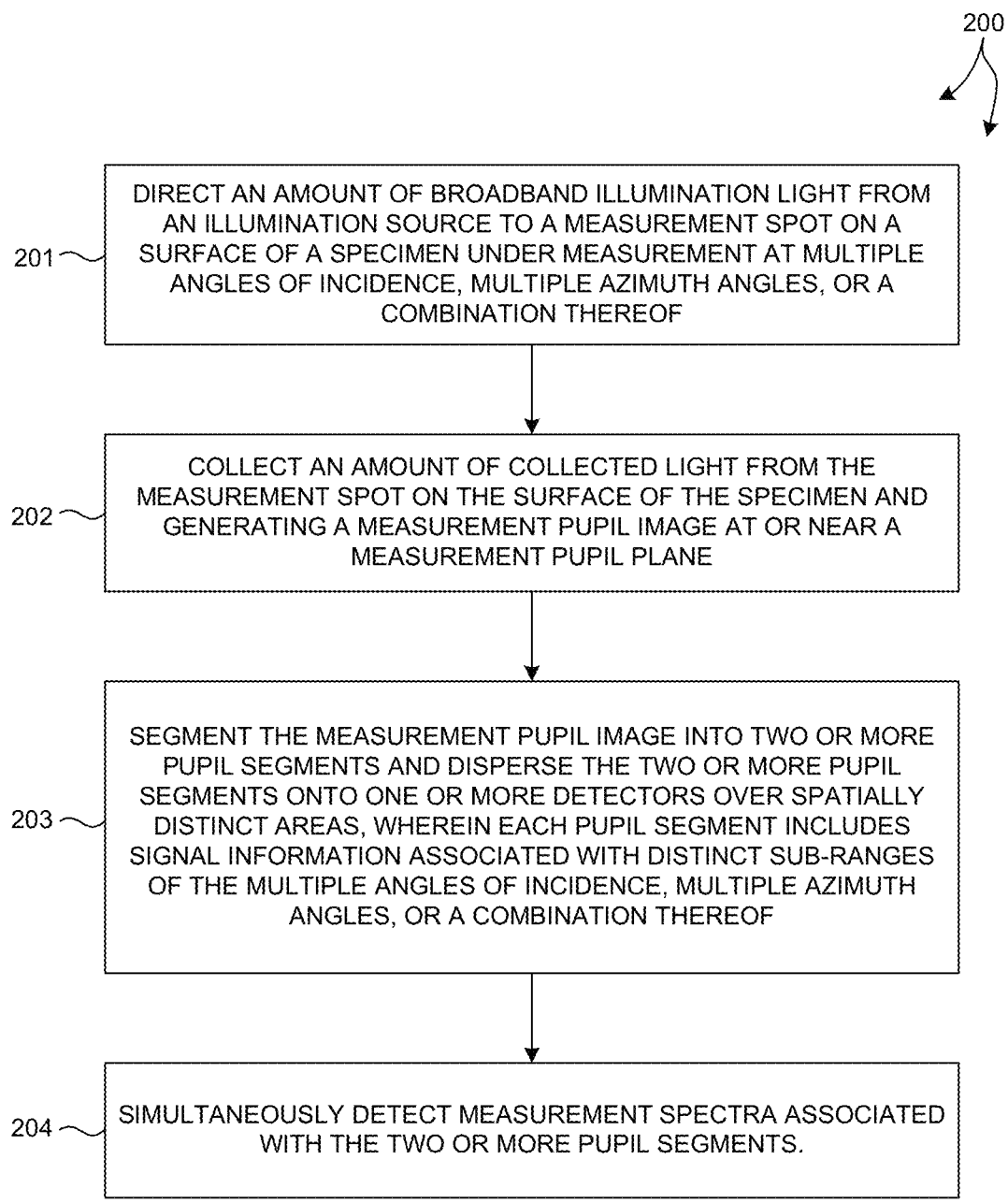
FIG. 11 illustrates a method 200 of performing simultaneous spectroscopic measurements of one or more structures over a broad range of angles of incidence, azimuth angles, or both, in at least one novel aspect as described herein.

FIG. 11 illustrates a method 200 of performing spectroscopic measurements in at least one novel aspect. Method 200 is suitable for implementation by a metrology system such as metrology system 100 illustrated in FIG. 1 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 201, an amount of broadband illumination light from an illumination source is directed to a measurement spot on a surface of a specimen under measurement at multiple angles of incidence, multiple azimuth angles, or a combination thereof.

In block 202, an amount of light is collected from the measurement spot on the surface of the specimen and a measurement pupil image is generated at or near a measurement pupil plane.

In block 203, the measurement pupil image is segmented into two or more pupil segments and the two or more pupil segments are dispersed onto one or more detectors over spatially distinct areas. Each pupil segment includes signal information associated with distinct sub-ranges of the multiple angles of incidence, multiple azimuth angles, or a combination thereof.

In block 204, measurement spectra associated with the two or more pupil segments are simultaneously detected.

Exemplary measurement techniques that may be configured as described herein include, but are not limited to spectroscopic ellipsometry (SE), including Mueller matrix ellipsometry (MMSE), rotating polarizer SE (RPSE), rotating polarizer, rotating compensator SE (RPRC), rotating compensator, rotating compensator SE (RCRC), spectroscopic reflectometry (SR), including polarized SR, unpolarized SR, spectroscopic scatterometry, scatterometry overlay, beam profile reflectometry, both angle-resolved and polarization-resolved, beam profile ellipsometry, single or multiple discrete wavelength ellipsometry, etc. In general, any metrology technique that includes a wide range of angular information in the measurement signals may be contemplated, individually, or in any combination. For example, any SR or SE technique applicable to the characterization of semiconductor structures, including image based metrology techniques, may be contemplated, individually, or in any combination.

In a further embodiment, system 100 includes one or more computing systems 130 employed to perform measurements of actual device structures based on spectroscopic measurement data collected in accordance with the methods described herein. The one or more computing systems 130 may be communicatively coupled to the spectrometer. In one aspect, the one or more computing systems 130 are configured to receive measurement data 170 associated with measurements of the structure of specimen 120.

It should be recognized that one or more steps described throughout the present disclosure may be carried out by a single computer system 130 or, alternatively, a multiple computer system 130. Moreover, different subsystems of system 100 may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometers in any manner known in the art. For example, the one or more computing systems 130 may be coupled to computing systems associated with the spectrometers. In another example, the spectrometers may be controlled directly by a single computer system coupled to computer system 130.

The computer system 130 of metrology system 100 may be configured to receive and/or acquire data or information from the subsystems of the system (e.g., spectrometers and the like) by a transmission medium that may include wireline and/or wireless portions. In this manner, the transmission medium may serve as a data link between the computer system 130 and other subsystems of system 100.

Computer system 130 of metrology system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral results obtained using the spectrometers described herein may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an estimated parameter value 171 determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Figure 10:
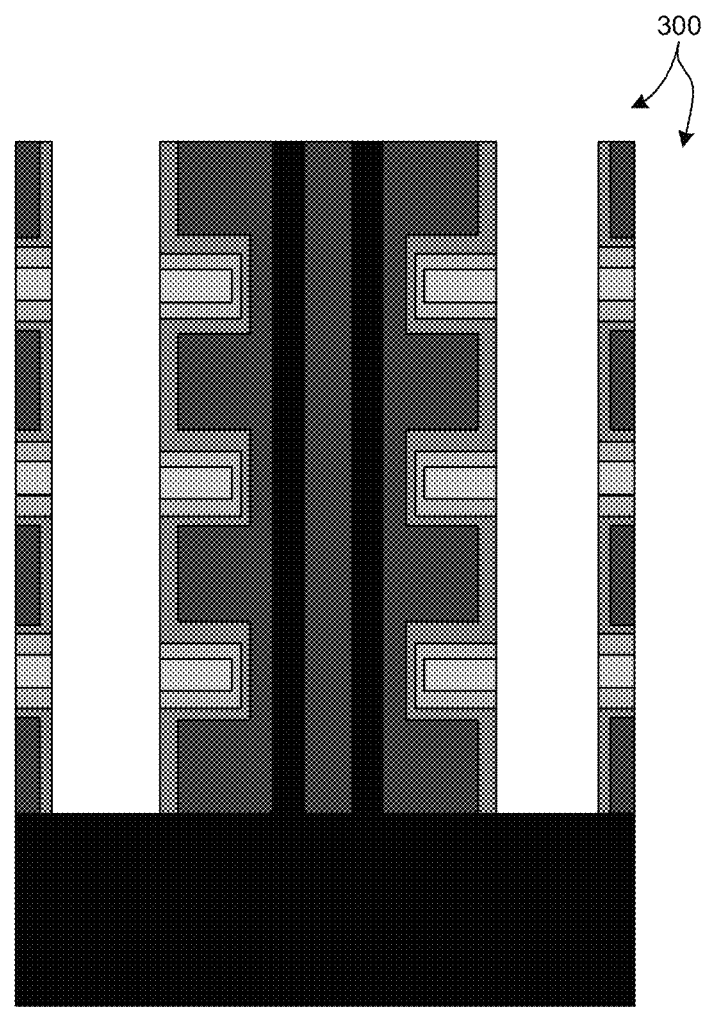
FIG. 10 depicts an exemplary high aspect ratio NAND structure 300 that suffers from low light penetration into the structure(s) being measured.

In another aspect, the methods and systems for spectroscopic metrology of semiconductor devices described herein are applied to the measurement of high aspect ratio (HAR) structures, large lateral dimension structures, or both. The described embodiments enable optical critical dimension (CD), film, and composition metrology for semiconductor devices including three dimensional NAND structures, such as vertical-NAND (V-NAND) structures, dynamic random access memory structures (DRAM), etc., manufactured by various semiconductor manufacturers such as Samsung Inc. (South Korea), SK Hynix Inc. (South Korea), Toshiba Corporation (Japan), and Micron Technology, Inc. (United States), etc. These complex devices suffer from low light penetration into the structure(s) being measured. FIG. 10 depicts an exemplary high aspect ratio NAND structure 300 that suffers from low light penetration into the structure(s) being measured. A spectroscopic ellipsometer with broadband capability and wide ranges of AOI, azimuth angle, or both, having simultaneous spectral band detection as described herein is suitable for measurements of these high-aspect ratio structures. HAR structures often include hard mask layers to facilitate etch processes for HARs. As described herein, the term "HAR structure" refers to any structure characterized by an aspect ratio that exceeds 10:1 and may be as high as 100:1, or higher.

In yet another aspect, the measurement results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor measurement system that may be used for measuring a specimen within any semiconductor processing tool (e.g., an inspection system or a lithography system). The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
one or more illumination sources configured to generate an amount of broadband illumination light;
an illumination optics subsystem configured to direct the amount of illumination light from the illumination source to a measurement spot on a surface of a specimen under measurement at multiple angles of incidence, multiple azimuth angles, or a combination thereof;
a collection optics subsystem configured to collect an amount of collected light from the measurement spot on the surface of the specimen, the collection optics subsystem having a measurement pupil;
one or more detectors each having a planar, two-dimensional surface sensitive to incident light; and a pupil segmentation and dispersion device configured to segment an image of the measurement pupil into two or more pupil segments and disperse the two or more pupil segments onto the one or more detectors over spatially distinct areas, wherein each pupil segment includes signal information associated with distinct sub-ranges of the multiple angles of incidence, multiple azimuth angles, or a combination thereof.

2. The metrology system of claim 1, wherein the pupil segmentation and dispersion device comprises:
a first diffractive element having an incidence surface located in an optical path of the collection optics subsystem at or near an image plane of the measurement pupil, wherein a first pupil segment is a portion of the collected light incident on the incidence surface of the first diffractive element; and
a second diffractive element having an incidence surface located in the optical path of the collection optics subsystem at or near the image plane of the measurement pupil, wherein a second pupil segment is a portion of the collected light incident on the incidence surface of the second diffractive element, wherein a normal to the incidence surface of the first diffractive element is oriented at a first angle with respect to a normal to the incidence surface of the second diffractive element.

3. The metrology system of claim 2, wherein each of the first diffractive element and the second diffractive element is a reflective grating structure, a transmissive grating structure, or a dispersive prism structure.

4. The metrology system of claim 3, wherein an axis angle associated with the first angle between the first diffractive element and the second diffractive element is oriented parallel to a blaze direction of the first diffractive element.

5. The metrology system of claim 3, wherein an axis angle associated with the first angle between the first diffractive element and the second diffractive element is oriented perpendicular to a blaze direction of the first diffractive element.

6. The metrology system of claim 3, wherein an axis angle associated with the first angle between the first diffractive element and the second diffractive element is oriented at an oblique angle with respect to a blaze direction of the first diffractive element.

7. The metrology system of claim 2, wherein the pupil segmentation and dispersion device further comprises:
a third diffractive element having an incidence surface located in the optical path of the collection optics subsystem near the image plane of the measurement pupil, wherein a third pupil segment is a portion of the collected light incident on the incidence surface of the third diffractive element, wherein a normal to the incidence surface of the first diffractive element is oriented at a second angle with respect to a normal to the incidence surface of the third diffractive element.

8. The metrology system of claim 7, wherein an axis angle associated with the second angle between the first diffractive element and the third diffractive element is equal in magnitude and opposite the direction of the axis angle associated with the first angle between the first diffractive element and the second diffractive element.

9. The metrology system of claim 3, wherein a grating pitch of the first diffractive element is different from a grating pitch of the second diffractive element.

10. The metrology system of claim 1, wherein the pupil segmentation and dispersion device is configurable within the metrology system, interchangeable with another pupil segmentation and dispersion device, or both.

11. The metrology system of claim 1, wherein a first of the one or more detectors includes two or more different surface areas each having different photosensitivity, wherein the two or more different surface areas are aligned with a direction of wavelength dispersion across the surface of the first detector.

12. The metrology system of claim 1, wherein a second of the one or more detectors measures background noise.

13. The metrology system of claim 1, wherein the amount of broadband illumination light includes a range of wavelengths including infrared, visible, and ultraviolet wavelengths.

14. The metrology system of claim 1, wherein the metrology system is configured as a spectroscopic ellipsometer, a spectroscopic reflectometer, or a combination thereof.

15. The metrology system of claim 1, further comprising:
a computing system configured to generate an estimated value of a parameter of interest of the specimen under measurement based on an analysis of the output of the one or more detectors.

16. A metrology system comprising:
an illumination optics subsystem configured to direct the amount of broadband illumination light from an illumination source to a measurement spot on a surface of a specimen under measurement at multiple angles of incidence, multiple azimuth angles, or a combination thereof;
a collection optics subsystem configured to collect an amount of collected light from the measurement spot on the surface of the specimen, the collection optics subsystem having a measurement pupil;
one or more detectors each having a planar, two-dimensional surface sensitive to incident light;
a first diffractive element having an incidence surface located in an optical path of the collection optics subsystem near an image plane of the measurement pupil, wherein a first pupil segment is a portion of the collected light incident on the incidence surface of the first diffractive element, wherein the first diffractive element disperses the first pupil segment over a first photosensitive area of the one or more detectors; and
a second diffractive element having an incidence surface located in the optical path of the collection optics subsystem near the image plane of the measurement pupil, wherein a second pupil segment is a portion of the collected light incident on the incidence surface of the second diffractive element, wherein the second diffractive element disperses the second pupil segment over a second photosensitive area of the one or more detectors that is spatially distinct from the first photosensitive area, and wherein a normal to the incidence surface of the first diffractive element is oriented at a first angle with respect to a normal to the incidence surface of the second diffractive element.

17. The metrology system of claim 16, wherein each of the first diffractive element and the second diffractive element is a reflective grating structure, a transmissive grating structure, or a dispersive prism structure.

18. The metrology system of claim 16, wherein a first of the one or more detectors includes two or more different surface areas each having different photosensitivity, wherein the two or more different surface areas are aligned with a direction of wavelength dispersion across the surface of the first detector.

19. A method comprising:
directing an amount of broadband illumination light from an illumination source to a measurement spot on a surface of a specimen under measurement at multiple angles of incidence, multiple azimuth angles, or a combination thereof;

collecting an amount of collected light from the measurement spot on the surface of the specimen and generating a measurement pupil image at or near a measurement pupil plane;

segmenting the measurement pupil image into two or more pupil segments and dispersing the two or more pupil segments onto one or more detectors over spatially distinct areas, wherein each pupil segment includes signal information associated with distinct sub-ranges of the multiple angles of incidence, multiple azimuth angles, or a combination thereof; and simultaneously detecting measurement spectra associated with the two or more pupil segments.

20. The method of claim 19, wherein the segmenting and dispersing of a first of the two or more pupil segment involves a first diffractive element having an incidence surface located in an optical path of the collection optics subsystem near an image plane of the measurement pupil, and wherein the segmenting and dispersing of a second of the two or more pupil segment involves a second diffractive element having an incidence surface located in the optical path of the collection optics subsystem near the image plane of the measurement pupil, wherein a normal to the incidence surface of the first diffractive element is oriented at a first angle with respect to a normal to the incidence surface of the second diffractive element.

21. The method of claim 19, wherein the specimen under measurement is a three dimensional NAND structure or a dynamic random access memory structure.

\* \* \* \* \*